United States Patent
Bystrov et al.

(10) Patent No.: US 9,519,990 B2
(45) Date of Patent: Dec. 13, 2016

(54) IMAGE DISPLAY APPARATUS

(75) Inventors: Daniel Bystrov, Hamburg (DE); Torbjoern Vic, Hamburg (DE); Heinrich Schulz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 286 days.

(21) Appl. No.: 14/125,167

(22) PCT Filed: Jun. 5, 2012

(86) PCT No.: PCT/IB2012/052818
§ 371 (c)(1),
(2), (4) Date: Dec. 10, 2013

(87) PCT Pub. No.: WO2012/176085
PCT Pub. Date: Dec. 27, 2012

(65) Prior Publication Data
US 2014/0111508 A1   Apr. 24, 2014

(30) Foreign Application Priority Data

Jun. 21, 2011   (EP) .................................... 11305775

(51) Int. Cl.
G06T 7/00      (2006.01)
G06T 15/00     (2011.01)
G06F 19/00     (2011.01)

(52) U.S. Cl.
CPC ............. *G06T 15/00* (2013.01); *G06F 19/321* (2013.01); *G06F 19/3406* (2013.01); *G06T 7/0012* (2013.01); *G06T 7/0079* (2013.01)

(58) Field of Classification Search
None
See application file for complete search history.

(56) References Cited

U.S. PATENT DOCUMENTS 7,899,222 B2     3/2011  Rinck et al.
2005/0168474 A1  8/2005  Truyen
(Continued)

FOREIGN PATENT DOCUMENTS

EP    1884898 A2    2/2008
WO    2006052681 A1 5/2006

OTHER PUBLICATIONS

Bondiau, P-Y., et al.; Atlas-based Automatic Segmentation of MR Images: Validation Study on the Brainstem in Radiotherapy Context; 2005; Int. J. Radiation Oncology Biol. Phys.; 61(1)289-298.

(Continued)

*Primary Examiner* — Ryan M Gray

(57) ABSTRACT

The invention relates to an image display apparatus for displaying an image like a three-dimensional medical image of an object. A template providing unit (3) provides a template defining display parameters for displaying the image based on anatomical features of the object, and an anatomical feature detecting unit (4) detects an anatomical feature in the image. A display parameter determining unit (5) determines a display parameter defining, for example, a desired view, based on the detected anatomical feature and the template, and a display unit (8) displays the image by displaying, for example, the desired view, in accordance with the determined display parameter. This allows the image display apparatus to show the image on the display in a desired usual way as defined by the template, even if in the originally provided image the object is shown in an unusual way.

20 Claims, 6 Drawing Sheets

(56) References Cited

U.S. PATENT DOCUMENTS

2006/0228015 A1* 10/2006 Brockway ............ G06T 7/0012
                                                382/132
2009/0316975 A1   12/2009 Kunz et al.
2010/0100560 A1    4/2010 Bystrov et al.
2010/0295848 A1   11/2010 Grewer et al.
2012/0163687 A1*  6/2012 Plakas ................. G06T 7/0038
                                                382/131

OTHER PUBLICATIONS

Brown, M. S., et al.; Method for Segmenting Chest CT Image Data Using an Anatomical Model: Preliminary Results; 1997; IEEE Trans. on Medical Imaging; 16(6)828-839.

Crum, W. R., et al.; Non-rigid image registration: theory and practice; 2004; The British Journal of Radiology; 77: S140-S153.

Fechter, J., et al.; User-centered Development of Medical Visualization Applications: Flexible Interaction Through Communicating Application Objects; 1996; Comput. & Graphics; 20(6)763-774.

Huijun, M., et al.; A system Framework of Adaptive User Interface Development for Cartographic Visualization System; 2010; IEEE Trans. on Evnironmental Science and Information Application Technology; pp. 333-336.

Park, H., et al.; Construction of an Abdominal Probabilistic Atlas and its Application in Segmentation; 2003; IEEE Trans. on Medical Imaging; 22(4)483-492.

Stewart, B. K., et al.; Medical Image Databases and Informatics; 1998; IEEE Processing; vol. 2:29-33.

* cited by examiner

IMAGE DISPLAY APPARATUS

FIELD OF THE INVENTION

The invention relates to an image display apparatus, an image display method and an image display computer program for displaying an image of an object. The invention relates further to a template generation apparatus, a template generation method and a template generation computer program for generating a template defining display parameters for displaying an image.

BACKGROUND OF THE INVENTION

In radiotherapy planning workstations segmentations of anatomical structures are normally performed by loading, for example, a planning computed tomography (CT) data set or a planning magnetic resonance (MR) data set, wherein the anatomical structures can be manually or automatically delineated in the loaded planning data sets. Some radiotherapy planning workstations also enable to view the planning images in coronal or sagittal views or even to reformat a volumetric image to an oblique view by manual interactions. This requires many user interactions, in order to find the best view for an anatomical structure. For example, the planning data set generally comprises a stack of image slices, wherein the user normally browses the stack of image slices to find the anatomical structure of interest. Moreover, if the person, which is shown in the planning data set, has been positioned in an unusual way, while generating the planning data set, the user has to perform the delineation of the anatomical structures and the reviewing of the planning data set, in particular, the radiotherapy planning and/or a quality assurance procedure, with corresponding unusual images.

SUMMARY OF THE INVENTION

It is an object of the present invention to provide an image display apparatus, an image display method and an image display computer program for displaying an image of an object, which allow displaying an image such that it facilitates reviewing of the image. It is a further object of the present invention to provide a template generation apparatus, a template generation method and a template generation computer program for generating a template defining display parameters for displaying an image, wherein the generated template is usable by the image display apparatus, the image display method and the image display computer program.

In a first aspect of the present invention an image display apparatus for displaying an image of an object is presented, wherein the image display apparatus comprises:
- an image providing unit for providing an image of the object,
- a template providing unit for providing a template defining display parameters for displaying an image based on anatomical features of the object,
- an anatomical feature detecting unit for detecting an anatomical feature in the image,
- a display parameter determining unit for determining a display parameter based on the detected anatomical feature and the template, and
- a display unit for displaying the image in accordance with the determined display parameter.

Since the display unit displays the image in accordance with a display parameter, which has been determined based on an anatomical feature detected in a provided image and based on a template defining display parameters for displaying an image based on anatomical features of the object, the image can be shown on the display in a desired usual way as defined by the template, even if in the originally provided image the object is shown in an unusual way. Moreover, also if the provided image shows the object in a usual, normal way, anatomical features can be detected in this image and the image can be displayed in a desired way as defined by the template based on the template and the detected anatomical features. For example, if the provided image is a three-dimensional image data set like a three-dimensional CT image data set or a three-dimensional MR image data set, the template can define that a certain number and kind of different views, which show certain anatomical structures, i. e. anatomical features, in certain orientations and certain positions, of the three-dimensional image data set are displayed, wherein the display parameters can be determined based on anatomical features detected in the provided three-dimensional image data set such that the display unit displays the certain views with the certain anatomical structures in their certain orientations and positions within the respective view. The image display apparatus allows therefore displaying the provided image in a desired way as defined by the template such that reviewing the provided image by, for example, a radiologist, can be facilitated. Since the image display apparatus allows displaying the provided image in a desired way as defined by the template, also operations, which may be performed by a user based on the displayed image, like a segmentation operation performed by the user and a radiotherapy planning operation may be facilitated.

The image providing unit can be adapted to provide a two-dimensional image or a three-dimensional image data set of the object. The three-dimensional image data set can be, for example, a CT image data set, an MR image data set, an ultrasound image data set, a nuclear image data set like a positron emission tomography (PET) image data set or a single photon emission computed tomography (SPECT) image data set.

The object is preferentially a living being like a person or an animal. However, the object can also be a technical object and the image display apparatus can also be adapted to be used for, for instance, baggage inspection.

The image providing unit can be a storing unit in which the image is stored already and/or an image receiving unit for receiving the image via a wired or wireless data connection and for providing the received image. Moreover, the image providing unit can also be an image generation unit like a CT system, an MR system, an ultrasound imaging system, a nuclear imaging system, et cetera. Thus, the image display apparatus can also be regarded as a combination of an image generation unit for providing the image and the further units for displaying the generated provided image.

The display unit can be adapted to display the entire image in accordance with a determined display parameter. However, preferentially the display unit is adapted to display certain desired views like coronal or sagittal views of a provided three-dimensional image data set depending on the determined display parameter, i.e. depending on the detected anatomical features and the template. The anatomical feature detecting unit can be adapted to detect one or several anatomical features, and the display parameter determining unit can be adapted to determine one or several display parameters. A view of a provided three-dimensional image data set can be a slice image of the provided three-dimensional image data set, which may be rotated, scaled and/or translated.

It is preferred that the template providing unit is adapted to provide a template defining at least one of the following display parameters: at least one view, if the image is a volumetric image, to be displayed; level; window; contrast; the location of an anatomical structure with respect to the displayed image; the orientation of an anatomical structure with respect to the displayed image. For example, the display parameters can define one or several views, which should be displayed, like a coronal view, a sagittal view, an oblique view, et cetera, and the display parameters can further define, for instance, the location and/or the orientation of an anatomical structure within the respective view. Also the level, window, contrast and/or other viewing parameters of each view can be defined by the display parameters. In particular, the image can be a volumetric planning CT dataset or volumetric planning MR dataset, wherein different views of the planning data set should be displayed for planning purposes, especially for radiotherapy planning. Which views of the planning dataset are displayed with which viewing parameters can be defined by the display parameters provided by the template.

It is further preferred that the template providing unit is adapted to provide a template defining display parameters for displaying the image based on anatomical features and further based on a task related to the displaying of the image, wherein the image display apparatus further comprises a task providing unit for providing a task and wherein the display parameter determining unit is adapted to determine a display parameter based on the template, the detected anatomical feature and the provided task. Thus, for different tasks different templates can be provided, which define the display parameters depending on the respective anatomical features. The task providing unit can be, for example, an input unit for allowing a user to input a desired task. The task providing unit can also be adapted to retrieve the task from the image, in particular, from header information of an image file representing the image. For example, a task can be to review the prostate in a three-dimensional image data set provided by the image providing unit. The template can define that the prostate should be displayed in the center of a view of the provided three-dimensional image data set. The anatomical feature detecting unit can therefore detect the prostate in the provided three-dimensional image data set, and display parameters defining that the detected prostate is displayed in the center of a view of the provided image are determined by the display parameter determining unit, wherein the display unit displays the view with the centered prostate in accordance with the determined display parameters.

In a preferred embodiment, the image is provided as an image file containing header information, wherein the template providing unit is adapted to provide a template defining display parameters for displaying the image based on anatomical features and further based on the header information and wherein the display parameter determining unit is adapted to determine a display parameter based on the template, the detected anatomical feature and the header information. For example, the header information can provide information about the imaging modality, the age, the gender, the expected disease, et cetera, wherein the template can provide display parameters based on this header information.

In an embodiment, the template providing unit is adapted to provide a template defining display parameters for displaying the image based on anatomical features and further based on significance values assigned to the anatomical features, the significance values defining a degree of consideration of the respective anatomical feature while determining the display parameters; the anatomical feature detecting unit is adapted to detect several anatomical features; and the display parameter determining unit is adapted to determine a display parameter based on the template, the detected anatomical features and the significance values assigned to the anatomical features. In particular, the image providing unit can be adapted to provide a three-dimensional image data set as the image of the object; the template providing unit can be adapted to provide a template, which defines display parameters, which define a view of the three-dimensional image data set and positions of anatomical features within the defined view, based on the anatomical features of the object and based on significance values assigned to the anatomical features; the anatomical feature detecting unit can be adapted to detect the anatomical features in the three-dimensional image data set; and the display parameter determining unit can be adapted to determine display parameters, which define a view of the three-dimensional image data set and positions of the detected anatomical features within the view, based on the detected anatomical features, the significance values assigned to the detected anatomical features and the template, wherein the display parameter determining unit can be adapted to consider the detected anatomical features in accordance with the respective assigned significance value defining the respective degree of consideration. For example, the display parameter determining unit can be adapted to determine display parameters, i. e., in this example, the display parameter determining unit can generate a view, such that a term is minimized, which depends on deviations of the current positions of the anatomical features in the generated view from the respective positions defined by the template and which considers the significance value of the respective anatomical feature, wherein the term decreases, if the deviations decrease. In particular, the term can depend on weighted squared or weighted absolute differences between the current positions of the anatomical features in the generated view and the respective positions defined by the template, wherein the weights can depend on, in particular, can be, the respective significance values.

It is further preferred that the anatomical feature detecting unit is adapted to apply a segmentation procedure to the image for detecting an anatomical feature in the image. In particular, the anatomical feature detecting unit is adapted to register an anatomical atlas with the image for segmenting the image. This allows determining the anatomical features reliably in a relatively simple way.

In a preferred embodiment, the anatomical feature detecting unit is adapted to detect anatomical features in several images, wherein the image display apparatus further comprises an input unit for allowing a user to input desired display parameters defining the displaying of the images and a desired display parameters storing unit for storing the desired display parameters for the several images such that for several images corresponding several display parameters can be provided, and wherein the template providing unit is adapted to generate a template depending on the several stored desired display parameters and the anatomical features detected in the corresponding several images. Thus, it can be observed how a user like a radiologist generally wants to see a provided image, i.e. it can be observed, for example, which views of a three-dimensional image data set a user prefers, wherein based on the observation and the anatomical features in the provided image one or several templates can be generated. Preferentially, also the respective task, which can be provided by a task providing unit, in particular, which can be input by the user, and/or further information like header information of a file containing the respective provided image can be considered for generating the respective template. A template can therefore be generated by training such that, after the training phase has been completed, future provided images are displayed as desired by the user by displaying the image in accordance with the generated trained template.

In a further aspect of the present invention a template generation apparatus for generating a template defining display parameters for displaying an image is presented, wherein the template generation apparatus comprises:
  an image providing unit for providing several images of the object,
  an anatomical feature detecting unit for detecting anatomical features in the images,
  an input unit for allowing a user to input desired display parameters defining a displaying of the images,
  a desired display parameters storing unit for storing the desired display parameters for the several images,
  a template generation unit for generating a template depending on the several stored desired display parameters and the anatomical features detected in the corresponding several images.

In an embodiment, the template generation unit is adapted to generate a template, which defines display parameters for displaying the image based on anatomical features and further based on significance values assigned to the anatomical features, depending on the several stored desired display parameters and the anatomical features detected in the corresponding several images, wherein the significance values define a degree of consideration of the respective anatomical feature while determining the display parameters by using the generated template. In particular, the image providing unit can be adapted to provide several three-dimensional image data sets as images of the object and the anatomical feature detecting unit can be adapted to detect anatomical features in the provided three-dimensional image data sets. The input unit allows the user to input desired display parameters defining how each provided three-dimensional image data set should be displayed. Preferentially, the desired display parameters define at least a desired view, which may be an initially provided view like an initially provided coronal or sagittal view and which may be rotated, scaled and/or translated by the user, and positions of the detected anatomical features in the desired view. For each of the detected anatomical features in the desired view an average position and a variation value are determined. The average position of the respective anatomical feature is, for example, an arithmetic mean, a geometric mean, a median or another average value. The average position defines the average of the positions of the same anatomical feature in the desired view, which has been defined by the user for the different provided three-dimensional image data sets. The variation value is indicative of the variation of the position of the respective anatomical feature in the desired view of the several three-dimensional image data sets. The variation value is, for example, a standard deviation or a median deviation. To each anatomical feature a significance value can be assigned depending on the variation value of the respective anatomical feature, wherein the larger the variation value, i. e. the larger the positions of the respective anatomical features vary in the input desired views of the several three-dimensional image data sets, the smaller the significance value. The generated template preferentially comprises the input desired view, the positions of the anatomical features within the desired view defined by the determined average positions, and the significance values of the anatomical features.

In a further aspect of the present invention an image display method for displaying an image of an object is presented, wherein the image display method comprises:
  providing an image of the object by an image providing unit,
  providing a template defining display parameters for displaying an image based on anatomical features of the object by a template providing unit,
  detecting an anatomical feature in the image by an anatomical feature detecting unit,
  determining a display parameter based on the detected anatomical feature and the template by a display parameter determining unit, and
  displaying the image in accordance with the determined display parameter by a display unit.

In a further aspect of the present invention, a template generation method for generating a template defining display parameters for displaying an image is presented, wherein the template generation method comprises:
  providing several images of the object by an image providing unit,
  detecting anatomical features in the images by an anatomical feature detecting unit,
  allowing a user to input desired display parameters defining a displaying of the images by an input unit,
  storing the desired display parameters for the several images by a desired display parameters storing unit,
  generating a template depending on the several stored desired display parameters and the anatomical features detected in the corresponding several images by a template generation unit.

In a further aspect of the present invention an image display computer program for displaying an image of an object is presented, wherein the image display computer program comprises program code means for causing an image display apparatus as defined in claim 1 to carry out the steps of the image display method as defined in claim 12, when the image display computer program is run on a computer controlling the image display apparatus.

In a further aspect of the present invention a template generation computer program for generating a template defining display parameters for displaying an image imaging is presented, wherein the template generation computer program comprises program code means for causing a template generation apparatus as defined in claim 10 to carry out the steps of the template generation method as defined in claim 13, when the template generation computer program is run on a computer controlling the template generation apparatus.

It shall be understood that the image display apparatus of claim 1, the template generation apparatus of claim 10, the image display method of claim 12, the template generation method of claim 13, the image display computer program of claim 14 and the template generation computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
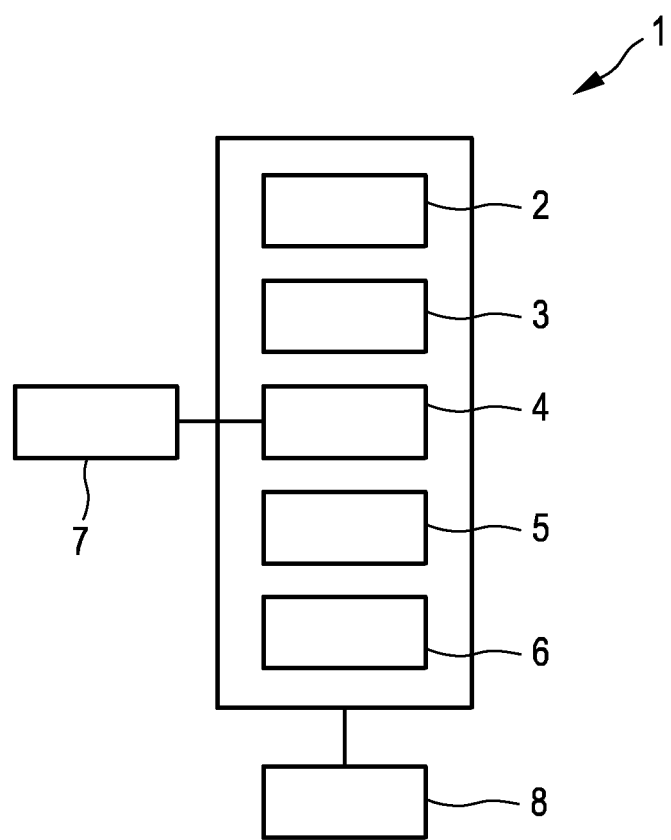
FIG. 1 shows schematically and exemplarily an embodiment of an image display apparatus for displaying an image of an object.

FIG. 1 shows schematically and exemplarily an image display apparatus for displaying an image of an object. The image display apparatus 1 comprises an image providing unit 2 for providing an image of the object. In this embodiment, the object is a person and the image providing unit 2 is adapted to provide a three-dimensional image data set like a three-dimensional CT image data set or a three-dimensional MR image data set as the image of the person. The image providing unit 2 is a storing unit, in which the three-dimensional image data set is stored already. In another embodiment, the image providing unit 2 can also be a receiving unit for receiving the three-dimensional image data set via a wired or wireless data connection and for providing the received three-dimensional image data set. The image providing unit can also be an image generating unit like a CT imaging system, an MR imaging system, a nuclear imaging system, an ultrasound imaging system, et cetera.

The image display apparatus 1 further comprises a template providing unit 3 for providing a template defining display parameters for displaying the three-dimensional image data set based on anatomical features of the person, an anatomical feature detecting unit 4 for detecting an anatomical feature in the provided three-dimensional image data set, and a display parameter determining unit 5 for determining a display parameter based on the detected anatomical feature and the template, wherein a display unit 8 displays the provided three-dimensional image data set, i.e. views of the three-dimensional image data set, in accordance with the determined display parameter.

The template providing unit 3 is adapted to provide a template defining at least one of the following display parameters: at least one view to be displayed; level; window; contrast; the location of an anatomical structure with respect to the displayed image, i.e., in this embodiment, the location of an anatomical structure with respect to a view of the provided three-dimensional image data set; the orientation of an anatomical structure with respect to the displayed image, i.e., in this embodiment, with respect to a view of the provided three-dimensional image data set.

In this embodiment, the display parameters define one or several views, which should be displayed, like a coronal view, a sagittal view, an oblique view, et cetera, and the location and/or the orientation of an anatomical structure within the respective view.

The template providing unit 3 is adapted to provide a template defining display parameters for displaying the image based on anatomical features and further based on a task related to the displaying of the image, wherein the image display apparatus 1 comprises a task providing unit 7 for providing a task and wherein the display parameter determining unit 5 is adapted to determine a display parameter based on the template, the detected anatomical feature and the provided task. Thus, for different tasks different templates can be provided, which define the display parameters depending on the respective anatomical features. In this embodiment, the task providing unit is an input unit 7 for allowing a user to input a desired task. For example, a graphical user interface can be provided, which allows a user to select a task from a predefined number of tasks by using the input unit 7. In another embodiment, the task providing unit can also be adapted to retrieve the respective task from header information of an image file representing the provided three-dimensional image data set.

For instance, the task can be reviewing the prostate of a person for radiation therapy planning. This task can be input by a radiologist via the input unit 7 or this task may be retrieved from the header information of a corresponding provided three-dimensional image data set. The template providing unit 3 can then provide a corresponding template, which defines, for example, that the prostate should be displayed in the center of a certain view, for example, in the center of a coronal view or a sagittal view of the provided three-dimensional image data set. The anatomical feature detecting unit 4 can then detect the prostate in the provided three-dimensional image data set and based on the template and the detected prostate the display parameter determining unit 5 can determine display parameters which define a certain view with the prostate in the center of the certain view, wherein the display unit 8 can show this certain view with the centered prostate in accordance with the determined display parameters.

The provided three-dimensional data set is preferentially provided as an image file containing header information, wherein the template providing unit 3 can also be adapted to provide the template based on the detected anatomical features, the provided task and the header information. Correspondingly, the display parameter determining unit 5 can be adapted to determine the display parameter based on the template, the detected anatomical feature and the header information. For example, the header information can provide information about the imaging modality, the age, the gender, the expected or the present disease, et cetera, wherein the template can provide display parameters based on this header information. This allows influencing the kind of displaying the provided three-dimensional image data set not only depending on the detected anatomical feature and a desired task, but also depending on further information provided by the three-dimensional image data set.

The anatomical feature detecting unit 4 is adapted to apply a segmentation procedure to the provided three-dimensional image data set for detecting one or several anatomical features in the image data set. In particular, the anatomical feature detecting unit 4 is adapted to register an anatomical atlas of the person with the three-dimensional image data set for segmenting the same.

The input unit 7 is preferentially further adapted to allow the user to input desired display parameters defining the displaying of the provided three-dimensional image data set, for example, for inputting desired views of the provided three-dimensional image data set. Preferentially, several three-dimensional image data sets are provided and for each of these provided three-dimensional image data sets a user can input desired display parameters defining the displaying of the image. The input desired display parameters for the provided several three-dimensional image data sets can then be stored in a desired display parameter storing unit 6. The anatomical feature detecting unit 4 can be adapted to detect anatomical features in the several provided three-dimensional image data sets and the template providing unit 3 can be adapted to generate a template depending on the several stored desired display parameters and the anatomical features detected in the corresponding three-dimensional image data sets. Thus, templates can be generated by training based on provided three-dimensional image data sets, for which desired display parameters have been defined by a user like a radiologist.

In this embodiment, the image display apparatus 1 is therefore not only adapted to display a provided three-dimensional image data set, but also to generate a template defining display parameters for displaying a three-dimensional image data set. However, in another embodiment the image display apparatus can also be adapted to only display provided three-dimensional image data sets, without providing the functionality of generating templates by training, wherein templates can be generated by a separate template generation apparatus for generating a template defining display parameters for displaying an image as schematically and exemplarily shown in FIG. 2.

Figure 2:
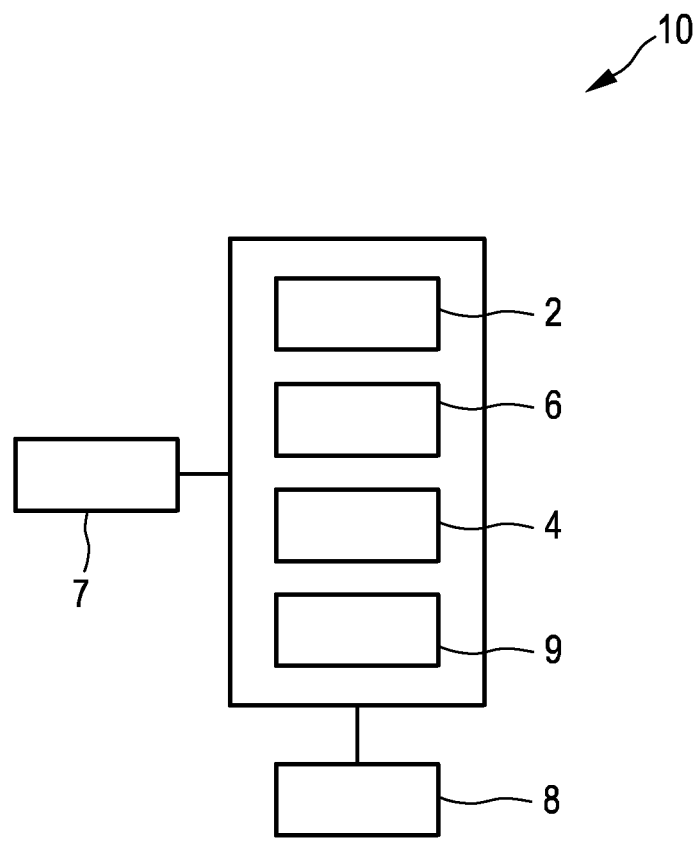
FIG. 2 shows schematically and exemplarily an embodiment of a template generation apparatus for generating a template defining display parameters for displaying an image.

The template generation apparatus 10 shown in FIG. 2 comprises an image providing unit 2 for providing an image of the object, which is, in this embodiment, a three-dimensional image data set of a person as described above. The template generation apparatus 10 further comprises an input unit 7 for allowing a user to input desired display parameters defining how the image should be displayed, i.e., in this embodiment, defining at least one view of the provided three-dimensional image data set; a desired display parameters storing unit 6 for storing the desired display parameters for several three-dimensional image data sets; an anatomical feature detecting unit 4 for detecting anatomical features in the several three-dimensional image data sets; and a template generation unit 9 for generating a template depending on the several stored desired display parameters and the anatomical features detected in the corresponding three-dimensional image data sets as described above. The input unit 7, the desired display parameter storing unit 6 and the anatomical features detection unit 4 are similar to the corresponding units described above with reference to FIG. 1. Also the display unit 8 of the template generation apparatus 10 corresponds to the display unit described above with reference to FIG. 1. The display unit 8 displays one or several views of the three-dimensional image data set in accordance with the desired display parameters input by the user by using the input unit 7.

In an embodiment, the template generation unit 9 is adapted to generate a template, which defines display parameters for displaying the image based on anatomical features and further based on significance values assigned to the anatomical features, depending on the several stored desired display parameters and the anatomical features detected in the corresponding several images, wherein the significance values define a degree of consideration of the respective anatomical feature while determining the display parameters by using the generated template. In particular, the image providing unit 2 can be adapted to provide several three-dimensional image data sets as images of the object and the anatomical feature detecting unit 4 can be adapted to detect anatomical features in the provided three-dimensional image data sets. The input unit 7 allows the user to input desired display parameters defining how each provided three-dimensional image data set should be displayed. Preferentially, the desired display parameters define at least a desired view, which may be an initially provided view like an initially provided coronal or sagittal view and which may be rotated, scaled and/or translated by the user, and positions of the detected anatomical features in the desired view. For each of the detected anatomical features in the desired view an average position and a variation value are determined. The average position of the respective anatomical feature is, for example, an arithmetic mean, a geometric mean, a median or another average value. The average position defines the average of the positions of the same anatomical feature in the desired view, which has been defined by the user for the different provided three-dimensional image data sets. The variation value is indicative of the variation of the position of the respective anatomical feature in the desired view of the several three-dimensional image data sets. The variation value is, for example, a standard deviation or a median deviation. To each anatomical feature a significance value can be assigned depending on the variation value of the respective anatomical feature, wherein the larger the variation value, i. e. the larger positions of the respective anatomical features vary in the input desired views of the several three-dimensional image data sets, the smaller the significance value. The generated template preferentially comprises the input desired view, the positions of the anatomical features within the desired view defined by the determined average positions, and the significance values of the anatomical features.

Correspondingly, the template providing unit 3 can be adapted to provide a template defining display parameters for displaying the image based on anatomical feature and further based on significance values assigned to the anatomical features; the anatomical feature detecting unit 4 can be adapted to detect several anatomical features; and the display parameter determining unit 5 can be adapted to determine a display parameter based on the template, the detected anatomical features and the significance values assigned to the anatomical features. In particular, the image providing unit 2 can be adapted to provide a three-dimensional image data set as the image of the object; the template providing unit 3 can be adapted to provide a template, which defines display parameters, which define a view of the three-dimensional image data set and positions of anatomical features within the defined view, based on the anatomical features of the object and based on significance values assigned to the anatomical features; the anatomical feature detecting unit 4 can be adapted to detect the anatomical features in the three-dimensional image data set; and the display parameter determining unit 5 can be adapted to determine display parameters, which define a view of the three-dimensional image data set and positions of the detected anatomical features within the view, based on the detected anatomical features, the significance values assigned to the detected anatomical features and the template, wherein the display parameter determining unit 5 can be adapted to consider the detected anatomical features in accordance with the respective assigned significance value defining the respective degree of consideration. For example, the display parameter determining unit 5 can be adapted to determine display parameters, i. e., in this example, the display parameter determining unit 5 can generate a view, such that a term is minimized, which depends on deviations of the current positions of the anatomical features in the generated view from the respective positions defined by the template and which considers the significance value of the respective anatomical feature, wherein the term decreases, if the deviations decrease. In particular, the term can depend on weighted squared or weighted absolute differences between the current positions of the anatomical features in the generated view and the respective positions defined by the template, wherein the weights can depend on, in particular, can be, the respective significance values.

Figure 3:
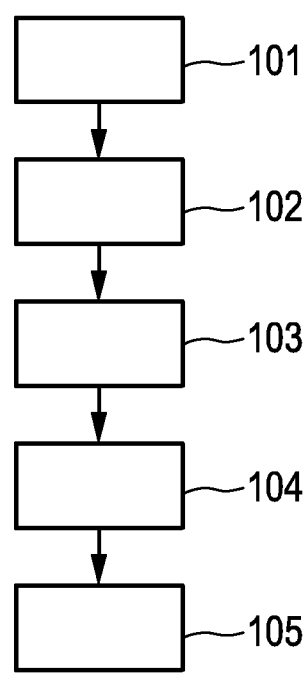
FIG. 3 shows a flowchart exemplarily illustrating an embodiment of an image display method for displaying an image of an object.

In the following an embodiment of an image display method for displaying an image of an object will exemplarily be described with reference to a flowchart shown in FIG. 3.

In step 101, a three-dimensional image data set of a person is provided by the image providing unit 2 and, in step 102, a template is provided by the template providing unit 3, which defines display parameters for displaying the provided three-dimensional image data set, in particular, for defining views of the three-dimensional image data set to be displayed, based on anatomical features of the person. In step 103, at least one anatomical feature is detected in the provided three-dimensional image data set by the anatomical feature detecting unit 4 and in step 104 a display parameter is determined based on the detected at least one anatomical feature and the template by the display parameter determining unit 5. The display parameter defines preferentially at least one view of the three-dimensional image data set to be displayed. In step 105, the three-dimensional image data set, i.e., in this embodiment, at least one view of the three-dimensional image data set, is displayed in accordance with the determined display parameter by the display unit 8.

Figure 4:
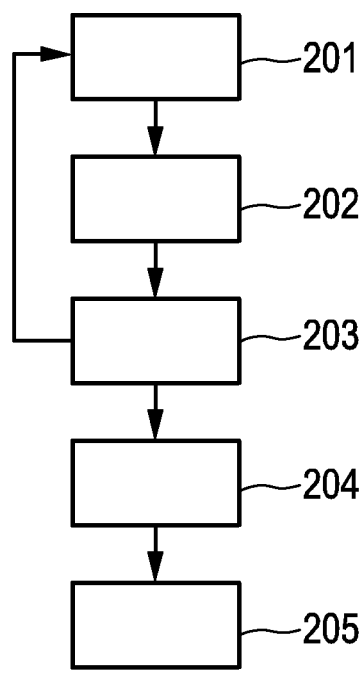
FIG. 4 shows a flowchart exemplarily illustrating an embodiment of a template generation method for generating a template defining display parameters for displaying an image.

In the following an embodiment of a template generation method for generating a template defining display parameters for displaying a three-dimensional image data set will exemplarily be described with reference to a flowchart shown in FIG. 4.

In step 201, a three-dimensional image data set of a person is provided by the image providing unit 2 and in step 202 a user can input desired display parameters defining how the provided three-dimensional image data set should be displayed via the input unit 7. In particular, the user can input display parameters defining at least one desired view to be displayed by the display unit 8. The input desired display parameters are then stored in the desired display parameters storing unit 6 in step 203. Steps 201 to 203 are preferentially repeated several times such that in the desired display parameters storing unit 6 several desired display parameters for several provided three-dimensional image data sets are provided. Repeatedly performing steps 201 to 203 leads to a training data set comprising assignments between three-dimensional image data sets and desired display parameters, wherein anatomical features can be detected in the several three-dimensional image data sets in step 204 and wherein the training data set with the detected anatomical features can be used in step 205 for generating a template by the template generation unit 9.

The template can also be generated based on further information like a provided task and/or header information retrieved from an image file containing the provided three-dimensional image data set.

The above described apparatuses and methods are preferentially adapted for radiation therapy planning. Radiation therapy planning often requires the exact delineation of anatomical structures and also an interactive procedure of quality assurance for the resulting segmentations. Beside medical and physical knowledge, this process requires a very good spatial sense of the user of the involved planning software. Therefore, the interface of a planning software should not distract the user by unnecessary, complex information. The display apparatus and method is therefore preferentially adapted for generating consistent sequences and sets of views for interactive image segmentation as well as for quality assurance. In particular, the input unit 7 can be adapted to allow a user to segment a desired anatomical structure in the displayed one or several views of the three-dimensional image data set.

The above described apparatuses and methods are preferentially adapted to train and derive required sets and sequences of views for a specific segmentation or quality assurance task, for example, to train and derive a required sequence of views required for the inspection of an automatically computed segmentation. In particular, the anatomical feature detecting unit can be adapted to perform an automatic image registration technique, which establishes a mapping of anatomical structures shown in the provided image onto an anatomical atlas. Afterwards, the significance of different anatomical positions, i.e. anatomical features, for a view can be analyzed using several training samples. A resulting significance map can be used to reproduce the same anatomy dependent view in a previously unseen three-dimensional image data set, in particular, in a previously unseen planning CT image data set or a previously unseen MR image data set. Beside the automatic computation of views, the apparatuses and methods can preferentially also train and derive viewing parameters like level and window, contrast et cetera.

Figure 5:
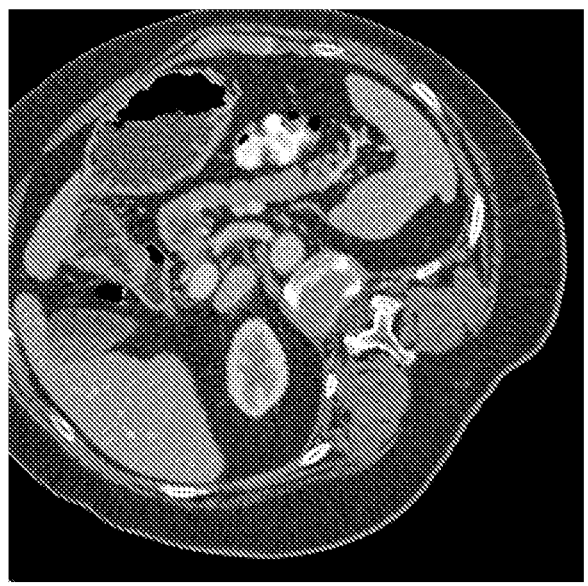
FIG. 5 shows schematically and exemplarily a slice of a provided three-dimensional image data set.
Figure 6:
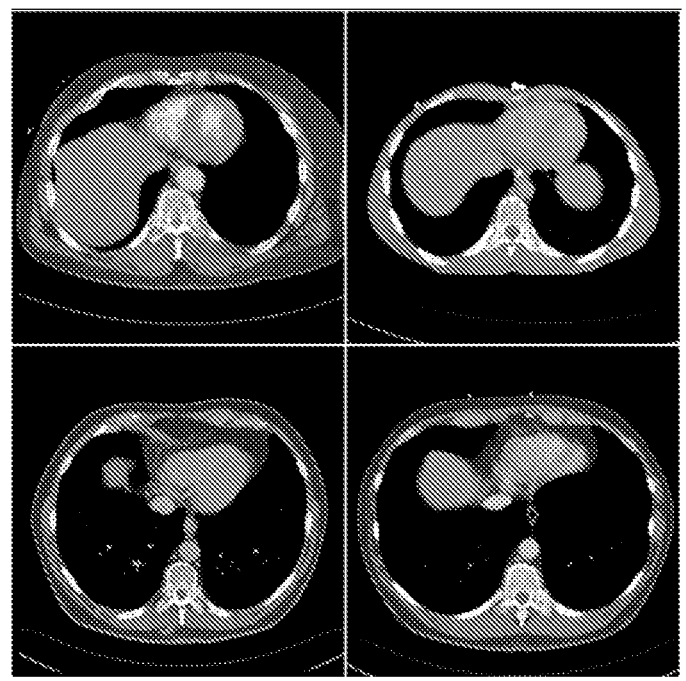
FIG. 6 shows schematically and exemplarily several views of a provided three-dimensional image data set.

FIG. 5 shows schematically and exemplarily a slice of a three-dimensional image data set of a person, which may be provided by the image providing unit 2. As can be seen in FIG. 5, the three-dimensional image data set shows an unusual placement of the person on the left side, which may cause difficulties in understanding the exact anatomical positions of the anatomical structures with respect to the person, i.e. which may cause difficulties in reviewing the provided three-dimensional image data set. Anatomical features can be detected in this provided three-dimensional image data set, display parameters can be determined based on the detected anatomical features and a provided template, and the display unit 8 can display views defined by the template in accordance with the determined display parameters as schematically and exemplarily shown in FIG. 6. Thus, independently of the placement of the person in the provided three-dimensional image data set the image display apparatus can display the desired views showing desired anatomical features in a desired orientation, i.e. consistent views not dependent on the person's positioning can be shown on the display unit 8, in order to support the spatial sense of the reviewing user.

The display apparatus and display method can be adapted to compute the significance of anatomical landmarks for an individual view using several training samples. Similarly, a dense significance field can be computed in the atlas space, instead of anatomical landmarks, using several training samples.

Specifically for radiation therapy planning an entire sequence or set of views can be displayed for the inspection of one or several anatomical structures in accordance with a provided template. The template can be determined by training at a clinical site using training samples, i.e. training data sets, or the template could already be included in the image display apparatus in the form of one or several templates.

The image display apparatus and method are preferentially adapted to automatically detect anatomical structures, i.e. anatomical features, in the provided images, which are preferentially planning images. Normally, this automatic detection does not need to be very precise and it can be sufficient to find a coarse and low dimensional transformation for registering the provided images with an anatomical atlas.

Although in the above described embodiments the image display apparatus comprises certain units only, the display apparatus can comprises further units for providing further functionalities. For example, the image display apparatus can further comprise units for planning a radiation therapy based on the displayed views of a provided planning image data set. In an embodiment, the display apparatus can therefore also be regarded as being a planning workstation.

If the image display apparatus comprises units for planning a radiation therapy, which include a unit for automatically segmenting an anatomical structure in a displayed image, this segmentation unit can also be used for detecting an anatomical feature in the provided three-dimensional image data set, which is used for determining the display parameters based on a provided template, i.e. the same segmentation unit can be used for segmenting for planning purposes and for segmenting for detecting an anatomical feature, which is used together with a provided template for displaying one or several views of a provided image data set.

The image display apparatus and image display method can be adapted for being used as a radiation therapy planning workstation, a medical image post-processing workstation for interactive medical image segmentation as well as a quality assurance workstation for assuring medical image segmentations.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Steps like the detection of anatomical features, the determination of display parameters and the generation of a template performed by one or several units or devices can be performed by any other number of units or devices. For example, steps 103 and 104 can be performed by a single unit or by any other number of different units. The above mentioned steps and/or the control of the image display apparatus in accordance with the image display method and/or the control of the template generation apparatus in accordance with a template generation method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an image display apparatus for displaying an image like a three-dimensional medical image of an object. A template providing unit provides a template defining display parameters for displaying the image based on anatomical features of the object, and an anatomical feature detecting unit detects an anatomical feature in the image. A display parameter determining unit determines a display parameter defining, for example, a desired view, based on the detected anatomical feature and the template, and a display unit displays the image by displaying, for example, the desired view, in accordance with the determined display parameter. This allows the image display apparatus to show the image on the display in a desired usual way as defined by the template, even if in the originally provided image the object is shown in an unusual way.

The invention claimed is:

1. An image display apparatus for displaying an image of an object, the image display apparatus comprising:
   an image providing unit for providing an image of the object,
   a template providing unit for providing a template defining display parameters for displaying an image based on anatomical features of the object and further based on significance values assigned to the anatomical features, the significance values defining a degree of consideration of the respective anatomical feature while determining the display parameters, the significance values being calculated based on a variation between a current position of the anatomical features of the object in the image and a defined position of the anatomical features of the object in the template,
   an anatomical feature detecting unit for detecting several anatomical features in the image,
   a display parameter determining unit for determining a display parameter based on the detected anatomical features, the template and the significance values assigned to the anatomical features to minimize a term between deviations corresponding to a view between the current position of the anatomical features of the object in the image and a defined position of the anatomical features of the object in the template, and
   a display unit for updating and displaying the updated image view in accordance with the determined display parameter.

2. The image display apparatus as defined in claim 1, wherein the template providing unit is adapted to provide a template defining at least one of the following display parameters: at least one view to be displayed; level; window; contrast; the location of an anatomical structure with respect to the displayed image; the orientation of an anatomical structure with respect to the displayed image.

3. The image display apparatus as defined in claim 1, wherein the template providing unit is adapted to provide a template defining display parameters for displaying the image based on anatomical features and further based on a task related to the displaying of the image, wherein the image display apparatus further comprises a task providing unit for providing a task and wherein the display parameter determining unit is adapted to determine a display parameter based on the template, the detected anatomical feature and the provided task.

4. The image display apparatus as defined in claim 1, wherein the image is provided as an image file containing header information, wherein the template providing unit is adapted to provide a template defining display parameters for displaying the image based on anatomical features and further based on the header information, and wherein the display parameter determining unit is adapted to determine a display parameter based on the template, the detected anatomical feature and the header information.

5. The image display apparatus as defined in claim 1, wherein
the image providing unit is adapted to provide a three-dimensional image data set as the image of the object,
the template providing unit is adapted to provide a template, which defines display parameters, which define a view of the three-dimensional image data set and positions of anatomical features within the defined view, based on the anatomical features of the object and based on the significance values assigned to the anatomical features,
the anatomical feature detecting unit is adapted to detect the anatomical features in the three-dimensional image data set,
the display parameter determining unit is adapted to determine display parameters, which define a view of the three-dimensional image data set and positions of the detected anatomical features within the view, based on the detected anatomical features, the significance values assigned to the detected anatomical features and the template, wherein the display parameter determining unit is adapted to consider the detected anatomical features in accordance with the respective assigned significance value defining the respective degree of consideration.

6. The image display apparatus as defined in claim 1, wherein the anatomical feature detecting unit is adapted to apply a segmentation procedure to the image for detecting an anatomical feature in the image.

7. The image display apparatus as defined in claim 6, wherein the anatomical feature detecting unit is adapted to register an anatomical atlas with the image for segmenting the image.

8. The image display apparatus as defined in claim 1, wherein the anatomical feature detecting unit is adapted to detect anatomical features in several images, wherein the image display apparatus further comprises:
an input unit for allowing a user to input desired display parameters defining the displaying of the images,
a desired display parameters storing unit for storing the desired display parameters for the several images such that for several images corresponding several display parameters can be provided, and
wherein the template providing unit is adapted to generate a template depending on the several stored desired display parameters and the anatomical features detected in the corresponding several images.

9. A template generation apparatus for generating a template defining display parameters for displaying an image, the template generation apparatus comprising:
one or more processors programmed to:
receive several images of the object,
detect anatomical features in the received images,
receive desired display parameters for displaying each of the received images,
a memory configured to store the desired display parameters and the detected anatomical features for the several received images,
wherein the one or more processors are further configured to:
generate a template, which defines display parameters for displaying the image based on the anatomical features and significance values assigned to each anatomical features based on the several stored desired display parameters and the anatomical features detected in the corresponding several images, the significance values defining a degree of a weight accorded each of the respective anatomical feature for determining the display parameters using the generated template,
determine the significance values based on variations among positions of each anatomical feature over the several images,
minimize deviations between current positions of the anatomical features and defined positions, as defined by the template, and
control a display device to update a displayed image based on the determined display parameter.

10. The template generation apparatus as defined in claim 9, wherein the one or more processors are further programed to:
receive a current image;
detect several anatomical features in the received image;
determine display parameters based on the detected anatomical features, the template, and the significance values assigned to the detected anatomical features; and
update the template using the current image;
wherein the template generation apparatus further includes a display apparatus configured to display the received image using the determined display parameter.

11. The template generation apparatus as defined in claim 9, wherein the one or more processors are further programed to:
receive a three-dimensional image data set as the image of the object;
detect the anatomical features in the three-dimensional image data set
determine display parameters based on the detected anatomical features, the significance values assigned to the detected anatomical features, and the template, the detected anatomical features being determined based on the respective assigned significance value defining the respective degree of consideration.

12. The template generation apparatus as defined in claim 9, further including:
an input configured to input desired display parameters defining the displaying of the images,
a memory configured to store the desired display parameters for the several images such that for several images corresponding several display parameters can be determined, and
wherein the one or more processors are further programmed to generate a template depending on the several stored desired display parameters and the anatomical features detected in the corresponding several images.

13. An image display method for displaying an image of an object, the image display method comprising:
providing an image of the object,
providing a template defining display parameters for displaying an image based on anatomical features of the object and further based on significance values assigned to the anatomical features, the significance values defining a degree of consideration of the respective anatomical feature while determining the display parameters, the significance values being determined based on a weighted relevance indicative of a variation between a current position of the anatomical features of the object in the image and a defined position of the anatomical features of the object by the template, detecting several anatomical features in the image, determining a display parameter based on the detected anatomical features the template and the significance values assigned to the anatomical features such that the determined display parameter minimizes deviations between current and template defined locations of one or more of the anatomical features, and updating and displaying the image in accordance with the determined display parameter.

14. A template generation method for generating a template defining display parameters for displaying an image, the template generation method comprising:

providing several images of the object, detecting anatomical features in the images, allowing a user to input desired display parameters defining a displaying of the images, storing the desired display parameters for the several images, generating a template, which defines display parameters for displaying the image based on anatomical features and further based on significance values assigned to the anatomical features, depending on the several stored desired display parameters and the anatomical features detected in the corresponding several images, the significance values defining a degree of consideration of the respective anatomical feature while determining the display parameters by using the generated template, the significance values being determined based on a weighted relevance indicative of variations between positions of the anatomical features in the image and in the template, such that the template is usable to update the display parameters for displaying the image to minimize a term indicative of deviations between current and templated defined positions of one or more of the anatomical features.

15. An image display non-transitory computer readable medium for displaying an image of an object, the image display non-transitory computer readable medium having executable instructions stored thereon for causing an image display apparatus to carry out the steps of the image display method as defined in claim 13, when the image display non-transitory computer readable medium is run on a computer controlling the image display apparatus.

16. A non-transitory computer readable medium having executable instructions stored thereon for causing one or more computers to carry out the steps of the template generation method as defined in claim 14.

17. A template generation apparatus for generating a template defining display parameters for displaying an image, the template generation apparatus comprising:

one or more processors configured to:

receive an image of the object;

receive providing a template defining display parameters for displaying an image based on anatomical features of the object and further based on significance values assigned to the anatomical features, the significance values defining a relative weight of each respective anatomical feature, the significance values being indicative of variations between positions of the anatomical features over images of a plurality of objects relative to the position of each anatomical feature defined by the template, detect several anatomical features in the image, determine display parameters which minimize a term indicative of deviations between current and template defined positions of one or more of the anatomical features of the object based on the detected anatomical features, the template, and the significance values assigned to the detected anatomical features, and a display apparatus configured to update and display the received image using the determined display parameter.

18. The template generation apparatus as defined in claim 17, wherein the one or more processors are further programed to:

receive a current image;

detect several anatomical features in the received image;

determine display parameters based on the detected anatomical features, the template, and the significance values assigned to the detected anatomical features; and update the template using the current image.

19. The template generation apparatus as defined in claim 17, wherein the one or more processors are further programed to:

receive a three-dimensional image data set as the image of the object;

detect the anatomical features in the three-dimensional image data set determine display parameters based on the detected anatomical features, the significance values assigned to the detected anatomical features, and the template, the detected anatomical features being determined based on the respective assigned significance value defining the respective degree of consideration.

20. The template generation apparatus as defined in claim 17, further including:

an input configured to input desired display parameters defining the displaying of the images, a memory configured to store the desired display parameters for the several images such that for several images corresponding several display parameters can be determined, and wherein the one or more processors are further programmed to generate a template depending on the several stored desired display parameters and the anatomical features detected in the corresponding several images.

* * * * *